United States Patent
Plicchi et al.

(10) Patent No.: US 6,405,084 B2
(45) Date of Patent: *Jun. 11, 2002

(54) IMPLANTABLE ATRIAL DEFIBRILLATOR APPARATUS

(75) Inventors: Gianni Plicchi, Bologna; Bruno Garberoglio, Turin; Guido Gaggini, Milan; Emanuela Marcelli, Macerata, all of (IT)

(73) Assignee: Sorin Biomedica Cardio, S.p.A. (IT)

( * ) Notice: Subject to any disclaimer, the term of this patent is extended or adjusted under 35 U.S.C. 154(b) by 0 days.

This patent is subject to a terminal disclaimer.

(21) Appl. No.: 09/843,511

(22) Filed: Apr. 25, 2001

Related U.S. Application Data

(63) Continuation of application No. 09/299,699, filed on Apr. 26, 1999, now Pat. No. 6,226,550.

(30) Foreign Application Priority Data

Jan. 28, 1999 (EP) .............................. 99830034

(51) Int. Cl.[7] .................................................. A61N 1/39
(52) U.S. Cl. .......................................................... 607/5
(58) Field of Search ............................... 607/4, 5, 6, 9, 607/14

(56) References Cited

U.S. PATENT DOCUMENTS

| 3,952,750 | A | 4/1976 | Mirowski et al. |
| 5,344,430 | A | 9/1994 | Berg et al. |
| 5,376,105 | A | 12/1994 | Hedberg |
| 5,800,465 | A | 9/1998 | Thompson et al. |
| 5,855,592 | A | 1/1999 | McGee et al. |
| 5,865,838 | A | 2/1999 | Obel et al. |
| 6,226,550 | B1 * | 5/2001 | Plicchi et al. .................. 607/6 |

OTHER PUBLICATIONS

PCT Notification of Trasmittal of the International Search Report for EP 99 83 0034.

* cited by examiner

Primary Examiner—George R. Evanisko
(74) Attorney, Agent, or Firm—Popovich & Wiles, P.A.

(57) ABSTRACT

An implantable defibrillator apparatus having a plurality of defibrillation electrodes which can be applied to the heart muscle in order to apply electric defibrillation shocks thereto, and a defibrillation-controller for selectively applying respective electric defibrillation shocks to the electrodes preferably sequentially in time and in synchronism with the QRS.

10 Claims, 1 Drawing Sheet

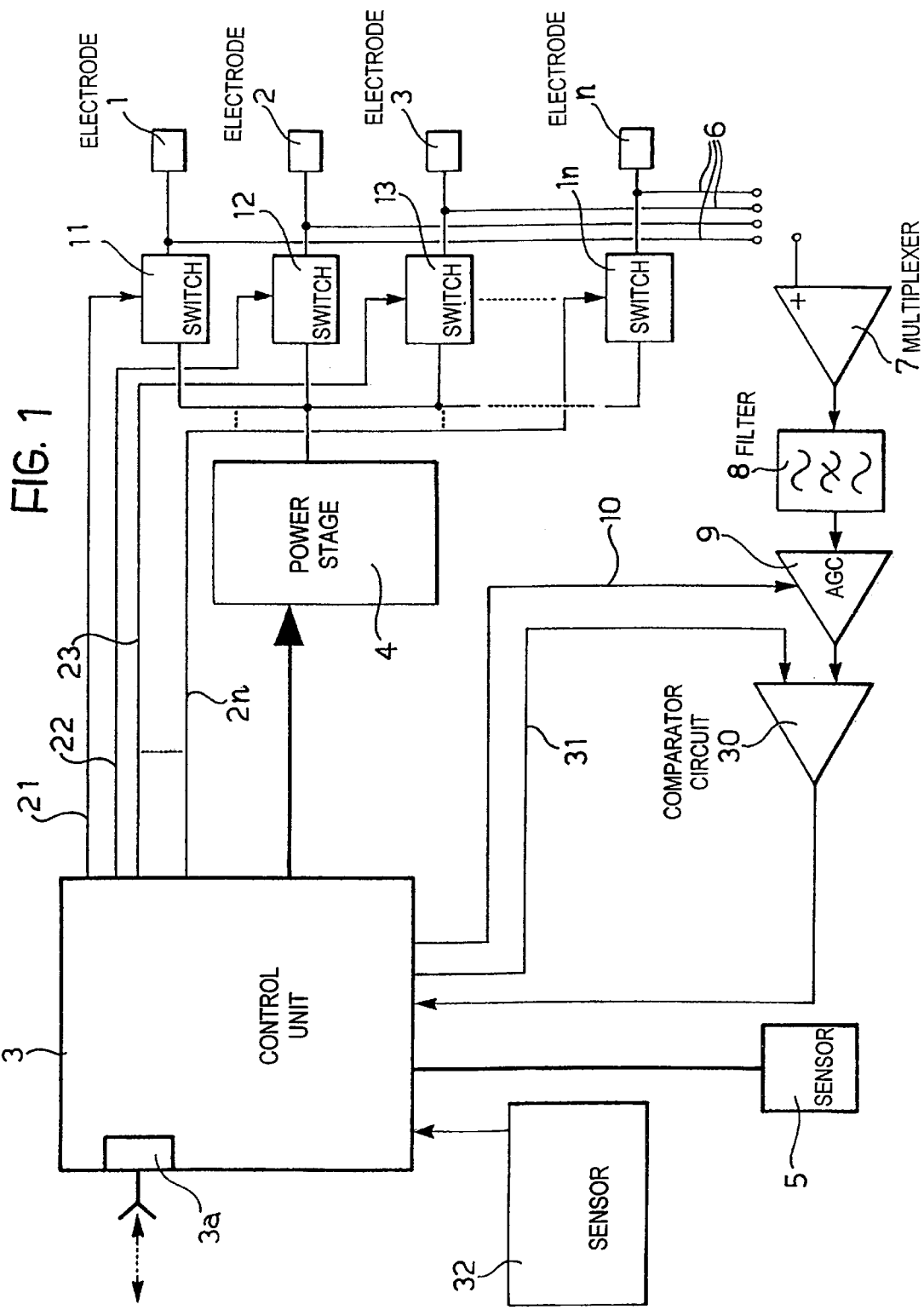

IMPLANTABLE ATRIAL DEFIBRILLATOR APPARATUS

This is a continuation of application Ser. No. 09/299,699, filed Apr. 26, 1999 now U.S. Pat. No 6,226,550, the contents of which are hereby incorporated herein by reference.

FIELD OF THE INVENTION

The present invention relates to defibrillation techniques, and in particular relates to atrial defibrillation.

BACKGROUND OF THE INVENTION

Atrial fibrillation (often referred to simply as AF), in its chronic and paroxysmal forms, constitutes the arrhythmia that is most frequent in the population, with a particularly high incidence (10%) in adults aged over 65 years. There is no pharmacological treatment which is sure to be effective and, as for all antiarrhythmic drugs, there is an increased probability of inducing serious ventricular proarrhythmia. In patients who are suffering from this condition to an incapacitating extent and who do not respond to the use of an average of two to three antiarrhythmia drugs, the subject of an alternative solution becomes important.

An implantable atrial defibrillator with an associated ventricular stimulation/sensing capability constitutes a recent treatment which is currently at the clinical evaluation stage. A defibrillator of this type is usually implanted by the insertion in the heart of two electrodes (leads) having large active surface areas and constituted by metal coils which are positioned along the outer wall of the right atrium and in the coronary sinus, whilst the metal container of the defibrillator can also operate as an active pole during discharge.

The basic object of defibrillation is to produce an electric field adequate to involve, anatomically, a significant portion of the myocardium of both atria, in order to depolarize, by means of the electric shock, a predominant number of myocardial cells which are subject to spontaneous, chaotic and non-synchronized electrical activity. Recent tests have shown the great importance of the distribution of the electric field in minimizing defibrillation energy and consequently voltage, muscle-stimulation and perception of pain, which constitutes the most important factor limiting the use of these devices.

SUMMARY OF THE INVENTION

The object of the present invention is to provide a defibrillator which can achieve an effective action antagonistic to fibrillation.

In one aspect, this invention is an implantable defibrillator apparatus comprising a plurality of defibrillation electrodes adapted to be applied to the heart muscle and to deliver electric defibrillation shocks thereto, the plurality of electrodes in communication with defibrillation-control means capable of selectively supplying voltage pulses to the electrodes, wherein the defibrillation control means controls the duration and interval of the voltage pulses and further wherein the voltage pulses produce electric defibrillation shocks sufficient to produce defibrillation. Preferably, the electric defibrillation shocks are sufficient to produce defibrillation synchronized with the heart's QRS, and the control unit can deliver defibrillation shocks to the electrodes in a desired time sequence. The control unit may selectively vary at least one characteristic of the electric defibrillation shocks, including the waveform of the defibrillation shock, the duration of the defibrillation shock, the interval between successive defibrillation shocks, and the electrodes to which a defibrillation shock is applied at any particular time. The apparatus may also comprise sensor means for detecting the occurrence of a fibrillation phenomenon, the sensor means being connected to the control unit and adapted to activate the application of defibrillation shocks. The sensor means may comprise respective sensing lines that connect the plurality of electrodes to the control unit to enable the electrodes to act both as defibrillation electrodes and as sensing electrodes. The apparatus may also comprise sensor means capable of detecting a ventricular electrogram. The control unit may synchronize the application of defibrillation shock during the QRS of the electrogram.

In another aspect, this invention is an implantable defibrillator apparatus comprising a plurality of defibrillation electrodes adapted to be applied to the heart muscle and to deliver electric defibrillation shocks thereto; the plurality of electrodes in communication with electronic switches; the electronic switches in communication with a power stage capable of supplying voltage pulses to the electrodes, wherein the power stage is connected to a control unit that controls the duration and interval of the voltage pulses and further wherein the voltage pulses are applied for a time sufficient to produce defibrillation.

In yet another aspect, this invention is a method of treating atrial fibrillation comprising providing a stimulating device having a plurality of electrodes; inserting the plurality of electrodes at desired locations in the heart; and applying defibrillation shocks to the plurality of electrodes in a desired sequence, thereby creating an electric field having a geometry designed for the patient's anatomy. Sensing atrial fibrillation may be done by means of the plurality of electrodes or by means of a specialized sensor.

BRIEF DESCRIPTION OF THE DRAWING

FIG. 1 shows a block diagram of the circuit structure of a multi-pole defibrillator according to the invention.

DETAILED DESCRIPTION OF PREFERRED EMBODIMENTS

Basically, the solution according to the invention enables the atrial defibrillation shock to be split up physically and over time so as to reduce the energy delivered.

In a preferred embodiment, the implantable atrial defibrillator of this invention comprises at least two electrodes that can be inserted permanently in the heart chambers. Each electrode has a surface area ranging from 50 to 100 mm$^2$. The electrodes permit the delivery of electric shocks in a programmable manner, sequentially in time, between any electrode or pole or group of electrodes or poles belonging to the same or to different leads, in order to defibrillate the fibrillating atria in an optimal manner.

The electrical characteristics of the shock and, in particular, the waveforms (single-phase, symmetric two-phase and asymmetric two-phase, etc.), the duration, and the interval between successive shocks (on the order of about 100 microseconds) can be programmed.

When atrial fibrillation has been confirmed by sensing of the chaotic atrial activity detectable by one or more poles of the same leads or by means of a specialized sensor, the sequence of defibrillation discharges is activated by sensing of the ventricular electrogram, detected by a suitable lead located in the right ventricle. This activation takes place in synchronism with the so-called QRS of the electrocardiograph signal to prevent dangerous proarrhythmia. The sequence has a programmable duration, by way of indication, no longer than 50 milliseconds, such that it is sure to be included within in the absolute refractory period of the ventricular myocardium.

Since the functional relationship between impedance and surface area of a conductor pole immersed in blood is hyperbolic, for surface areas greater than about 50 to 100 mm$^2$, reduced variations occur in impedance as a function of surface area. In the currently preferred solution for implementing the invention, a low shock voltage thus suffices to produce, at each of the above-described poles, a current density equal to that which requires voltages even three to four times greater in the single poles of large surface area which are used predominantly at the moment. It is consequently possible to achieve effective atrial defibrillation with reduced perception of pain, which is caused mainly by the voltage. The multi-pole configuration also permits the creation of an electric field of variable geometry designed for the patient's anatomy, which can further reduce the need for high voltages.

The invention will now be described with reference to FIG. 1, which shows a plurality of electrodes (or "poles"), indicated 1, 2, 3, ... n, that can be fitted in sites of the heart suitable for bringing about an effect antagonistic to fibrillation (defibrillation), particularly with regard to atrial fibrillation (AF), by the application of electric signals (shocks).

The structural characteristics of these electrodes, for example, the selection of constituent materials, any surface treatment, etc., are those currently used in known implantable defibrillators.

In particular, the term "electrode" or "pole" as used herein is intended to define any electrically-conductive member which can be associated with the heart muscle in a relationship suitable for the transmission of an electrical signal. Consequently, the electrodes or poles in question may either be configured as physically separate members which are thus intended to be fitted in distinct and separate respective myocardial sites, or may be associated in groups or sets with respective supporting structures (so-called "leads") so as to be fitted in respective myocardial sites separately (in the sense that each electrode or pole can transfer—and detect—a respective signal to—and from—the myocardium) but not independently, since the electrodes or poles of each group disposed on a respective lead are implanted simultaneously as a result of the implantation of the respective supporting element.

The apparatus may comprise two electrodes, or in more complex configurations, the number n may equal, for example, ten electrodes. Preferred numbers of electrodes typically range from three to five. Electrodes 1 to n may either be identical to one another or may have different shapes according to the sites in which they are to be positioned.

In general, electrodes 1 to n preferably have a surface area typically of the order of 50 mm$^2$ or more, for example, 100 mm$^2$. Since, as mentioned above, the functional relationship between impedance and surface area of a conductor pole immersed in blood is typically hyperbolic, with surface-area values of the type indicated, a low shock voltage (for example 50 to 100 volts) suffices to produce a current density in each of the electrodes equal to that which required the application of voltages even three to four times greater in the (single) electrodes of known implantable defibrillators.

The apparatus comprises defibrillation control means having power stage 4; electrodes 1, 2, 3, ... to n; electronic enabling switches 11, 12, 12, ..., in; and timing and control unit 37, whose operation is described as follows.

Power stage (the "high voltage" stage) 4 of the implantable defibrillator generates voltage pulses which are applied to electrodes 1, 2, 3, ... to n, via respective electronic enabling switches or control gates 11, 12, 13, ..., in.

Switches or control gates 11 to in are connected to respective enabling lines 21, 22, 23, ..., 2n, thus allowing the signals generated in power stage 4 to pass selectively towards electrodes 1, 2, ... n). Switches or control gates 11 to in communicate with and are controlled by timing and control unit 37, preferably provided with telemetering interface 37a of generally known type.

The control performed by control unit 37 by means of lines 21, 22, 23, ... 2n enables the characteristics of the defibrillation signals applied to the myocardium to be programmed, in particular with regard to the following characteristics:

the waveform: single-phase, symmetric two-phase and asymmetric two-phase, etc., the duration of each shock, the interval between successive shocks, and the ability to activate the defibrillation pulses in the various electrodes 1, 2, 3, ..., n sequentially in time (in accordance with a typical time-sharing scheme).

As a result, the above-described multi-pole configuration permits, in particular, the creation of an electric defibrillation field of variable geometry designed for the patient's anatomy, by virtue of the ability to program the emission of the control signals by control unit 37. This permits a further reduction in the intensity (in practice, the voltage) of the signals applied; this results in an ability to achieve effective atrial defibrillation with low pain perception since the latter is caused mainly by the voltage.

The defibrillation may be activated by sensing of the chaotic atrial activity in the presence of fibrillation, which may be detected by means of specialized sensor 5 of generally known type. However, in a particularly preferred embodiment of the invention, it is possible to replace and/or to supplement this conventional sensing with sensing performed by the electrodes 1, 2, 3, ... n themselves. Respective sensing lines, generally indicated 6, are provided for this purpose and enable the electrical signals indicative of the local myocardial activity at the respective implant site to be detected by the respective electrode so as to supply to control unit 37 a set of signals which enables control unit 37 to see and to identify the occurrence of a fibrillation phenomenon.

The block diagram of FIG. 1 shows multiplexer 7, that enables the signal coming from one or more of electrodes 1, 2, 3, ... n, to be detected selectively by the respective sensing line 6. After anti-noise filtering performed in filter 8 and automatic gain control performed in automatic gain-control circuit (AGC) 9 controlled by control unit 37 by means of line 10, the sensing signals thus detected reach comparator circuit 30. Here, the sensing signals are compared with a threshold level, which may be adaptively modifiable, and which is supplied by control unit 37 by means of line 31.

Finally, a sensor (of known type), indicated 32, can detect ventricular activity and can supply to the unit a corresponding synchronization signal such that control unit 37 can synchronize the application of the shock sequence by the electrodes 1 to n with the ventricular QRS.

Moreover, the various electronic components shown in the drawing (or at least those of low power) clearly may either be in the form of discrete blocks or components, or may be integrated in a single circuit.

According to known criteria, the sensing operation is regulated in a manner such as to prevent a sensing signal from being picked up from an electrode which is being used at the time in question for the application of a defibrillation signal. In particular, as already mentioned, the sequence of defibrillation discharges is activated by sensing of the ventricular electrogram detected by sensor 32, preferably located in the right ventricle, so as to have a programmable duration, by way of indication, no greater than 50 milliseconds, which is sure to be included within the absolute refractory period of the ventricular myocardium.

Naturally, the principle of the invention remaining the same, the details of construction and forms of embodiment may be varied widely with respect to those described and illustrated, without thereby departing from the scope of the present invention, as defined by the following claims.

What is claimed is:

1. An implantable atrial defibrillator apparatus comprising:
    a plurality of defibrillation electrodes adapted to be applied to the heart muscle of at least one atrium and to deliver electric defibrillation shocks thereto,
    first sensor means for detecting an occurrence of atrial fibrillation and for generating a first signal indicative thereof;
    second sensor means for detecting a ventricular electrogram and an absolute refractory period of the ventricular myocardium and generating a second signal indicative thereof;
    control means connected to receive the first and second signals for selectively supplying a defibrillation pulse sequence to the electrodes in response to the occurrence of atrial fibrillation, the defibrillation pulse sequence including a plurality of voltage pulses separated in time by a pulse interval, the pulse sequence being configured by the control means to have a time of duration no greater than the absolute refractory period of the ventricular myocardium as detected by the second sensor means, the control means being connected to supply the pulse sequence to the electrodes so that the pulses are applied to the heart muscle only during the absolute refractory period of the ventricular myocardium, the control means being adapted to selectively vary at least one characteristic of the voltage pulses, the at least one characteristic selected from the group of waveform of the voltage pulses, the duration of the voltage pulses, the interval between successive voltage pulses, and the electrodes to which a voltage pulse is applied at any particular time such that application of the defibrillation pulse sequence to the heart muscle creates an electric defibrillation field of variable geometry dependent on the selective variations of the at least one characteristic of the voltage pulses.

2. An apparatus according to claim 1, wherein the first and second sensor means comprise respective sensing lines that connect the plurality of electrodes to the control means to enable the plurality of electrodes to act both as defibrillation electrodes and as sensing electrodes.

3. An apparatus according to claim 1 wherein the plurality of defibrillation electrodes comprises three to five electrodes.

4. An implantable atrial defibrillator apparatus comprising:
    a plurality of defibrillation electrodes adapted to be applied to the heart muscle of at least one atrium and to deliver electric defibrillation shocks thereto;
    a first sensor configured to detect an occurrence of atrial fibrillation and to generate a first signal indicative thereof;
    a second sensor configured to detect a ventricular electrogram and an absolute refractory period of the ventricular myocardium and to generate a second signal indicative thereof;
    a control unit connected to receive the first and second signals, the control unit being configured to selectively supply a defibrillation pulse sequence to the electrodes in response to the occurrence of atrial fibrillation, the defibrillation pulse sequence including a plurality of voltage pulses separated in time by a pulse interval, the pulse sequence being configured by the control means to have a time of duration no greater than the absolute refractory period of the ventricular myocardium as detected by the second sensor means, the control means being connected to supply the pulse sequence to the electrodes so that the pulses are applied to the heart muscle only during the absolute refractory period of the ventricular myocardium, the control unit being configured to selectively vary at least one characteristic of the voltage pulses, the at least one characteristic selected from the group of waveform of the voltage pulses, the duration of the voltage pulses, the interval between successive voltage pulses, and the electrodes to which a voltage pulse is applied at any particular time such that application of the defibrillation pulse sequence to the heart muscle creates an electric defibrillation field of variable geometry dependent on the selective variations of the at least one characteristic of the voltage pulses.

5. An apparatus according to claim 4, wherein the voltage pulse interval is about 100 microseconds.

6. An apparatus according to claim 4, wherein an electrode of the plurality of electrodes has a surface area ranging from about 50 $mm^2$ to about 100 $mm^2$.

7. An apparatus according to claim 4, wherein the time of duration of the pulse sequence is no greater than 50 milliseconds.

8. An apparatus according to claim 4, wherein the first and second sensors comprise respective sensing lines that connect the plurality of electrodes to the control unit to enable the electrodes to act both as defibrillation electrodes and as sensing electrodes.

9. An apparatus according to claim 4 wherein the plurality of defibrillation electrodes comprises three to five electrodes.

10. A method of treating atrial fibrillation comprising:
    supplying a stimulating device having a control unit, a plurality of defibrillation electrodes, a first sensor configured to detect an occurrence of atrial fibrillation and a second sensor configured to detect a ventricular electrogram;
    implanting the stimulating device so that the plurality of electrodes are applied to the heart muscle of at least one atrium, the first sensor is positioned to detect an occurrence of atrial fibrillation and the second sensor is positioned to detect a ventricular electrogram;
    detecting at the first electrode an occurrence of atrial fibrillation;
    detecting at the second electrode a ventricular electrogram and an absolute refractory period of the ventricular myocardium;
    supplying to the control unit first and second signals indicative of the occurrence of atrial fibrillation and of the ventricular electrogram, respectively;
    generating, in response to the first and second signals, a defibrillation pulse sequence comprising a plurality of voltage pulses separated in time by a pulse interval, the pulse sequence being configured by the control unit to have a time of duration no greater than the absolute refractory period of the ventricular myocardium as detected by the second sensor; and applying the pulse sequence to the plurality of electrodes so that the voltage pulses are applied to the heart muscle only during the absolute refractory period of the ventricular myocardium, such that the control unit selectively varies at least one characteristic of the voltage pulses, the at least one characteristic selected from the group of the waveform, the duration, the interval between voltage pulses, and the sequence of activating voltage pulses to various electrodes and such that application of the defibrillation pulse sequence to the heart muscle creates an electric defibrillation field of variable geometry dependent on the selective variations of the at least one characteristic of the voltage pulses.

* * * * *